(12) United States Patent
Galindro et al.

(10) Patent No.: US 8,835,672 B2
(45) Date of Patent: Sep. 16, 2014

(54) MANUFACTURE OF A TRIIODINATED CONTRAST AGENT

(75) Inventors: Jose Manuel Galindro, Sao Marcos (PT); Ana Cristina Cruz, Lisbon (PT); João José Bandarra, Lisbon (PT); William Heggie, Palmela (PT)

(73) Assignee: Hovione Inter Limited, Lucerne (CH)

( * ) Notice: Subject to any disclaimer, the term of this patent is extended or adjusted under 35 U.S.C. 154(b) by 0 days.

(21) Appl. No.: 14/128,782

(22) PCT Filed: Feb. 2, 2012

(86) PCT No.: PCT/GB2012/000109
§ 371 (c)(1),
(2), (4) Date: Dec. 23, 2013

(87) PCT Pub. No.: WO2012/175903
PCT Pub. Date: Dec. 27, 2012

(65) Prior Publication Data
US 2014/0155648 A1    Jun. 5, 2014

(30) Foreign Application Priority Data
Jun. 24, 2011    (PT) .......................................... 105770

(51) Int. Cl.
| | | |
|---|---|---|
| C07C 67/02 | (2006.01) | |
| C07C 233/00 | (2006.01) | |
| C07C 231/18 | (2006.01) | |
| C07C 231/24 | (2006.01) | |
| C07C 231/02 | (2006.01) | |
| C07C 235/16 | (2006.01) | |

(52) U.S. Cl.
CPC ............. *C07C 231/02* (2013.01); *C07C 231/18* (2013.01); *C07C 231/24* (2013.01); *C07C 235/16* (2013.01)
USPC .......................................... 560/254; 564/153

(58) Field of Classification Search
None
See application file for complete search history.

(56) References Cited

U.S. PATENT DOCUMENTS

| | | | | |
|---|---|---|---|---|
| 4,001,323 A | * | 1/1977 | Felder et al. .................. | 564/153 |
| 7,282,607 B2 | * | 10/2007 | Lorenzini et al. ............. | 564/153 |
| 7,368,101 B2 | * | 5/2008 | Anelli et al. ................. | 424/9.454 |

FOREIGN PATENT DOCUMENTS

| | | |
|---|---|---|
| GB | 1472050 A | 4/1977 |
| WO | 00/50385 A1 | 8/2000 |
| WO | 02/44132 A1 | 6/2002 |

OTHER PUBLICATIONS

International Preliminary Report on Patentability, Application No. PCT/GB2012/000109 dated Dec. 24, 2013.
International Search Report, Application No. PCT/GB2012/000109 dated Mar. 7, 2012.

* cited by examiner

*Primary Examiner* — Karl J Puttlitz
(74) *Attorney, Agent, or Firm* — MacMillan, Sobanski & Todd, LLC

(57) ABSTRACT

A new compound, (S)-5-(2-acetoxypropanamido)-2,4,6-triiodoisophthalic acid, of formula II (S)-5-(2-acetoxypropanamido)-2,4,6-triiodoisophthalic acid. Said new compound is of use for the production of triiodinated contrast agent, especially Iopamidol, with low content of acetyl and hydroxyacetyl analogs. The new compound may be formed from 5-amino-2,4,6-triiodoisophtalic acid by acylating with (S)-1-chloro-1-oxopropan-2-yl acetate. The new compound may then be converted to the respective acid dichloride by reacting with a chlorinating reagent, which is a further object of the present invention, followed by the amidation with 2-amino-1,3-propanediol and acetate hydrolysis.

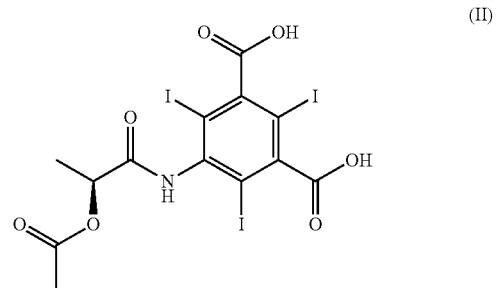

(S)-5-(2-acetoxypropanamido)-2,4,6-triiodoisophthalic acid

26 Claims, No Drawings

MANUFACTURE OF A TRIIODINATED CONTRAST AGENT

The present invention claims the benefit of the PCT/GB2012/000109 filed 2 Feb. May 2012, which claims priority to Ser. PT/105770 filed 24 Jun. 2011.

The present invention is related to a process for the manufacture of a triiodinated contrast agent, such as Iopamidol, via a new chemical compound.

BACKGROUND

Iopamidol is one of the most used non-ionic iodinated X-ray contrast agents. In the manufacture of Iopamidol a multi-step synthesis is involved.

Several methods have been disclosed in the literature for the synthesis of Iopamidol. The methods first described for the preparation of Iopamidol, as disclosed in GB1472050 and U.S. Pat. No. 4,001,323, introduced the chiral center by reacting 5-amino-2,4,6-triiodoisophthaloyl dichloride with (S)-1-chloro-1-oxopropan-2-yl acetate. One disadvantage appointed (see U.S. Pat. No. 7,282,607) to these methods is the introduction of the chiral center very early in the synthesis, however, it is more economically preferred to introduce the highly expensive reagent 2-amino-1,3-propanediol (serinol) as late as possible in the synthesis. In contrast other methods more recently described introduced the chiral center in the last steps of the synthesis, as disclosed in U.S. Pat. No. 7,282,607 and U.S. Pat. No. 7,368,101, including making esters of 5-amino-$N^1$,$N^3$-bis(1,3-dihydroxypropan-2-yl)-2,4,6-triiodoisophthalamide and other protecting strategies, followed by the reaction of the protected derivative with (S)-1-chloro-1-oxopropan-2-ylacetate. The last step of the synthesis removes all the groups introduced to protect the primary alcohols including the acetate from the chiral center thus affording Iopamidol. Such methods release a high quantity of by products, making these methods less economically and environmentally friendly, atomically speaking. To overcome this drawback a method that includes less "atom usage", as did the firstly described methods of GB1472050 and U.S. Pat. No. 4,001,323, is preferred. A method that uses fewer acyl chloride intermediates would also be preferred; as such methods would facilitate industrial operations.

Surprisingly, the method of the present invention meets the above needs and requirements by using 5-amino-2,4-6-triiodoisophatalic acid as a starting material and introducing the chiral center in the first stage of the process by reaction with (S)-1-chloro-1-oxopropan-2-yl acetate thus forming the new compound, (S)-5-(2-acetoxypropanamido)-2,4,6-triiodoisophthalic acid. Furthermore, the method via the new compound allows the synthetic route to triiodinated contrast agents, such as Iopamidol, to proceed without racemization, avoiding the use of protection/deprotection methodologies and introducing the highly expensive reagent serinol, immediately before the chemical step where Iopamidol is obtained. Moreover Iopamidol, is obtained in high purity, with a very low content of related process impurities such as acetyl and hydroxyacetyl analogs.

DESCRIPTION OF THE INVENTION

According to one aspect of the present invention, there is provided a new compound, (S)-5-(2-acetoxypropanamido)-2,4,6-triiodoisophthalic acid, of formula II presented below.

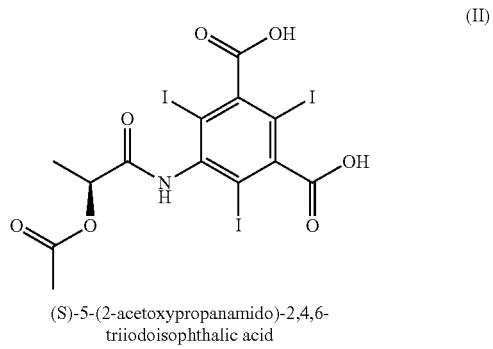 [SMILES: CC(=O)O[C@@H](C)C(=O)Nc1c(I)c(C(=O)O)c(I)c(C(=O)O)c1I]

(S)-5-(2-acetoxypropanamido)-2,4,6-triiodoisophthalic acid

According to a second aspect of the present invention, there is provided a process for the synthesis of Iopamidol via the new compound of formula II. Said process comprises reacting the new compound of formula II with a chlorinating agent forming the known compound 5-amino-2,4,6-triiodoisophthaloyl dichloride (formula III), followed by an amidation reaction with serinol, which after acetate hydrolysis provides Iopamidol, according to the scheme presented below.

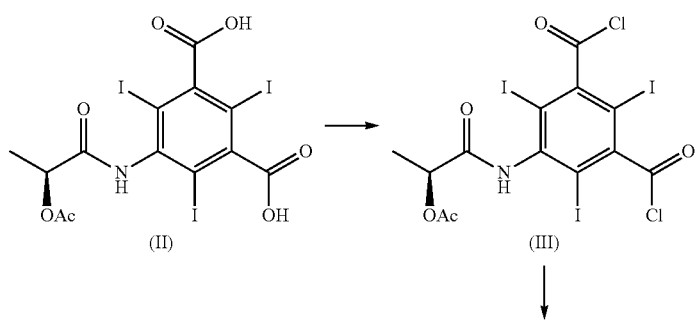

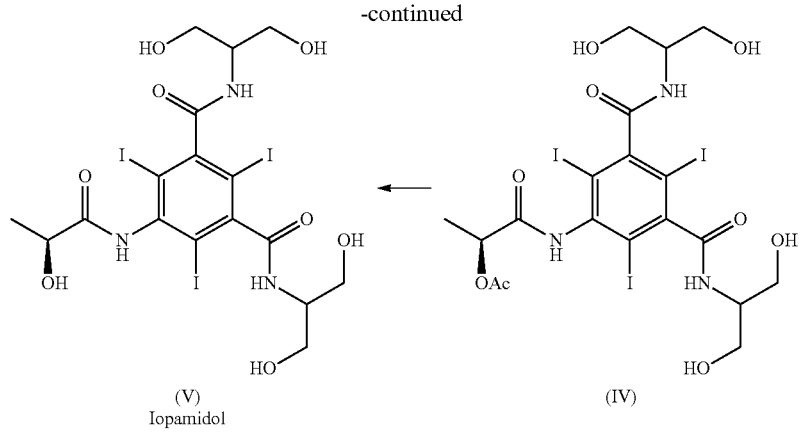

(V) Iopamidol (IV)

The amidation reaction and the acetate hydrolysis may both be carried out via methods described in the prior art.

According to a third aspect of the present invention, there is provided a process for the synthesis of the new compound of formula II. Said process comprises reacting 5-amino-2,4,6-triiodoisophtalic acid (formula I) with (S)-1-chloro-1-oxo-propan-2-yl acetate thus forming the new compound (S)-5-(2-acetoxypropanamido)-2,4,6-triiodoisophthalic acid of formula II, according to the scheme presented below.

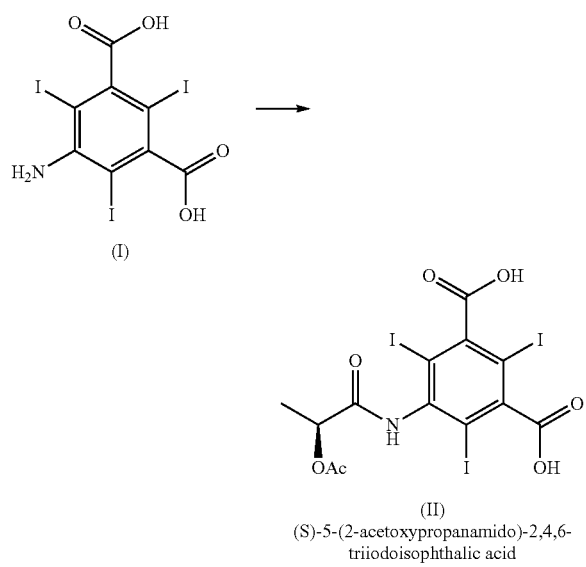

(II)
(S)-5-(2-acetoxypropanamido)-2,4,6-triiodoisophtalic acid

The acylation reaction is carried out in a suitable solvent such as an aprotic polar solvent, preferably dimethylacetamide (DMA), in which 5-amino-2,4,6-triiodoisophtalic acid may be dissolved. From 1 ml to 5 ml of DMA may be used per 1 gram of 5-amino-2,4,6-triiodoisophtalic acid. To this solution an acyl halide, preferably an acyl chloride such as (S)-1-chloro-1-oxopropan-2-yl acetate (also known as (S)-(−)-2-acetoxypropionyl chloride, which is commercially available) may be added without further purification. Preferably the acyl halide is added at a temperature of from 15° C. to 25° C. The ratio of the acyl halide relative to the amine may be of at least 1.5:1 (equivalents). The resulting reaction mixture may be heated at a temperature of from 40° C. to 60° C., preferably from 48° C. to 52° C., most preferably at about 50° C. The heated reaction mixture may be maintained at the desired temperature for a set period of time from 5 to 9 hours, preferably about 8 hours. After this time, the resulting reaction mixture may be stirred at a temperature of from 15° C. to 25° C. until the desired level of conversion is achieved. After the reaction is considered to be completed, the mixture may be slowly added to water to promote the precipitation of the compound of formula II giving a good dispersion of the solids in the mixture. The ratio of water relative to the polar aprotic solvent may be from 5:1 to 16:1. The suspension formed may be stirred for up to 5 hours at a temperature of from 15° C. to 25° C., preferably at a temperature of about 22° C., after which the solids may be separated by filtration and washed with water. The product may be dried under vacuum, preferably at a temperature of below about 50° C. The process for the synthesis of the new compound of formula II, according to the present invention enables the production of the new compound of formula II in good yield and in high purity (by HPLC, up to 99.9%).

To synthesize Iopamidol using the new compound of formula II, the new compound is dissolved in a suitable polar solvent such as acetonitrile, N-methylpyrrolidone or, preferably, DMA. The polar solvent may be used in a ratio of 5:1 relative to the compound of formula II. A suitable chlorinating agent, such as phosphorus pentachloride (which is preferred by comparison with for example the less environmental friendly thionyl chloride) is added portion-wise to the solution to promote the formation of the dichloride of formula III. Alternatively other suitable halidating agents may be used to form the dihalide equivalent of formula III. The thus formed reaction mixture is stirred at a temperature of from 25° C. to 50° C., preferably from 38° C. to 42° C., most preferably at about 40° C., until the desired level of conversion is attained. After the reaction is considered to be complete the mixture is added to water previously cooled to a temperature of from 10° C. to 0° C., preferably 5° C. to 0° C., preferably over a period of time of over one hour with stirring. Preferably the reaction mixture is added to the water in a ratio of 2:1 relative to the quantity of the polar solvent. This enables isolation of the acid dichloride of the compound of formula II (or the equivalent dihalide). The white precipitate formed is separated by filtration and washed with water. The wet solid can be further purified according to procedures known and commonly used by those skilled in the art, for example, by suspension in a mixture of water and isopropyl alcohol. The quantity of water added at this stage is minimized to minimize the undesired hydrolysis reaction thus reducing the yield lost. The suspension of the white solid is stirred at temperature of below 25° C. to promote a more efficient wash of the suspended solids. The acid dichloride is separated from the mixture by filtration and the wet filter cake is rinsed with a suitable solvent, as for example isopropyl alcohol to wash out most of the water. The wet solid can be used directly without drying which constitutes another advantage of the present invention. The wet solid can be dried under vacuum at a temperature of from 25° C. to 45° C., preferably at 40° C. to 45° C. obtaining the known compound of formula III.

The compound of formula III (or the equivalent dihalide) is allowed to react with 2-amino-1,3-propanediol. The reaction with 2-amino-1,3-propanediol may be carried out as per the methods disclosed in the literature, such as after dissolution in DMA and in the presence of a base. After isolation the compound of formula IV is obtained in good yield with a purity of 98% in area by HPLC, which includes about 2% of Iopamidol (formula V) that is formed during the process. Finally, the compound of formula IV thus obtained may be converted to Iopamidol. Conversion of the compound of formula IV to Iopamidol may be carried out as per the methods described in the literature, Iopamidol may be obtained after isolation by crystallization from ethanol in high purity and with a very low content of impurities B (formula VI) and C (acetyl analog—formula VII), respectively of 0.002% and 0.004% (area by HPLC, Iopamidol concentration of 10 mg/ml).

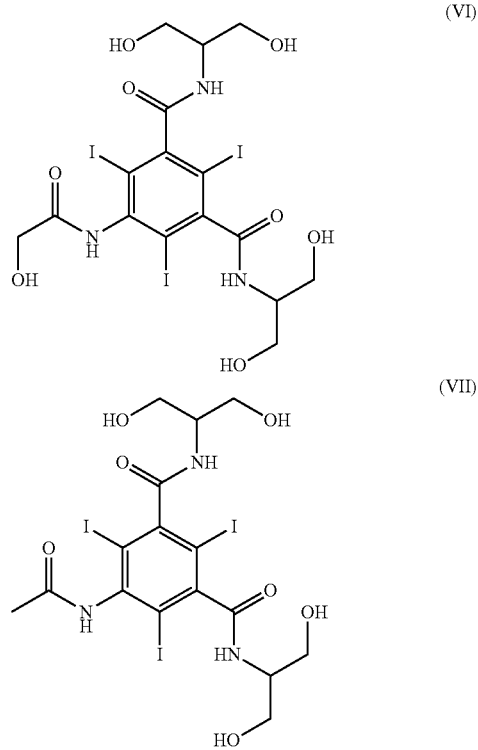

The preparation of the new compound of formula II and the respective process of the invention following the conversion to Iopamidol is illustrated and clarified by the description of the non-limiting examples described hereafter.

EXAMPLE 1

Preparation of (S)-5-(2-acetoxypropanamido)-2,4,6-triiodoisophthalic Acid (S)-1-chloro-1-oxopropan-2-yl acetate (0.75 ml, 5.91 mmol) was added drop-wise to a solution of 5-amino-2,4,6-triiodoisophthalic acid (1.0 g, 1.79 mmol) in DMA (5 ml). The resulting mixture was stirred at about 50° C. for 5 hours and 20 minutes. 80 ml of water was added to the reaction mixture at room temperature after which the suspension formed was cooled to a temperature between 0° C. and 5° C. and stirred for 25 minutes at this temperature. The suspension was filtered and the solid washed with water. The product was dried in a vacuum oven at 40° C. to yield (S)-5-(2-acetoxypropanamido)-2,4,6-triiodoisophthalic acid (0.695 g, 1.03 mmol). The MS, $^1$H-NMR and $^{13}$C-NMR data are consistent with the structure for (S)-5-(2-acetoxypropanamido)-2,4,6-triiodoisophthalic acid.

Yield: 57.5%

HPLC Purity: 99.91%

(Column: µ Porasil 125 A 10 µm (300×3.9 mm). Mobile Phase: Hexane: Tetrahydrofuran [(80/20) (v/v)] and 0.05% of trifluoracetic acid. Wavelength: 254 nm;

Column temperature: 40° C.).

MS: ES$^+$ [M+H]$^+$ found 673.88, $C_{13}H_{11}I_3NO_7$ requires 673.77.

$^1$H-NMR: $\delta_H$ (400 MHz, DMSO-$d_6$) 10.11 (2H, s, C(O)O—H), 5.22 (1H, m, C—H), 2.12 (3H, s, COCH$_3$), 1.51 (3H, d, J 6.8, CHCH$_3$); $^{13}$C-NMR: $\delta_C$ (100 MHz, DMSO-$d_6$) 169.4 (C=O), 168.2 (C=O), 149.3 (2 Ar—C), 142.4 (1 Ar—C—N), 97.9 (2 Ar—C—I), 87.3 (1 Ar—C—I), 69.4 (C—O), 20.8 (CH$_3$), 17.5 (CH$_3$).

EXAMPLE 2

Preparation of (S)-5-(2-acetoxypropanamido)-2,4,6-triiodoisophthalic Acid (S)-1-chloro-1-oxopropan-2-yl acetate (37.4 ml, 295.4 mmol) was added slowly to a suspension of 5-amino-2,4,6-triiodoisophthalic acid (50.0 g, 89.5 mmol) in DMA (100 ml) at a temperature of between 25° C. and 29° C. The resulting mixture was heated to about 50° C. and stirred at this temperature for about 8 hours after which heating was removed and the mixture was stirred for about 14 hours at room temperature. The reaction mixture was added slowly over water (500 ml) with strong stirring at a temperature between 22° C. and 30° C. After addition 300 ml of water were added to the suspension. The suspension was stirred for 5 further hours at about 22° C. after which the white solid was filtered and washed with water previously cooled at about 5° C. twice (30 ml each time). The product was dried in a vacuum oven at about 5.0° C. to yield (S)-5-(2-acetoxypropanamido)-2,4,6-triiodoisophthalic acid (48.8 g, 72.5 mmol).

Yield: 81%

$[\alpha]_{436}^{20}$=−21.69° (99.25 mg/ml, Ethanol)

Purity by HPLC: 99.4% (HPLC conditions as used for example 1)

Melting point: 214.7° C. (with decomposition)

EXAMPLE 3

Preparation of (S)-1-((3,5-bis(chlorocarbonyl)-2,4,6-triiodophenyl)amino)-1-oxopropan-2-yl acetate Phosphorus pentachloride (37.1 g, 178.3 mmol) was added portion-wise to a solution of the (S)-5-(2-acetoxypropanamido)-2,4,6-triiodoisophthalic acid obtained in example 2 (40.0 g, 59.4 mmol) in DMA (200 ml). The reaction mixture was stirred at about 40° C. for 6 hours after which it was added drop-wise to water (400 ml) cooled to a temperature of between 0° C. and 5° C. with vigorous stirring over 1 hour. The resulting suspension was stirred one further hour at a temperature of between 0° C. and 5° C. and the white precipitate was filtered. The white solid was washed with water (80 ml) previously cooled to a temperature of between 0° C. and 5° C. The solid was re-suspended in a mixture of water (103 ml) and isopropanol (80 ml) and stirred at this temperature for 15 minutes. The suspension was warmed up to a temperature of between 20° C. and 25° C. and stirred at this temperature for 30 minutes and then cooled again to a temperature of between 0° C. and 5° C. and stirred for 15 minutes. The white precipitate was filtered and dried at a temperature of between 40° C. and 45° C. to yield (S)-1-((3,5-bis(chlorocarbonyl)-2,4,6-triiodophenyl)amino)-1-oxopropan-2-yl acetate as a white solid (32.4 g, 45.7 mmol).

Yield: 77.0%

HPLC Purity: 98.4% (HPLC conditions as used for example 1)

EXAMPLE 4

Preparation of (S)-1-((3,5-bis((1,3-dihydroxypropan-2-yl)carbamoyl)-2,4,6-triiodophenyl)amino)-1-oxopropan-2-yl acetate The preparation of (S)-1-((3,5-bis((1,3-dihydroxypropan-2-yl)carbamoyl)-2,4,6-triiodo-phenyl)amino)-1-oxopropan-2-yl acetate was carried taking as reference the procedures described in the literature. 20 g (28.2 mmol) of (S)-1-((3,5-bis(chlorocarbonyl)-2,4,6-triiodophenyl)amino)-1-oxopropan-2-yl acetate from example 3 was reacted with 2-amino-1,3-propanediol (6.4 g, 70.5 mmol) in DMA (100 ml) in the presence of triethylamine (10.0 ml, 71.4 mmol) at 50° C. for 6 hours. After complete reaction and removal of the salts by filtration, the solvent was distilled under vacuum at below 70° C. until a viscous oil was obtained. While the residue was still hot, alcohol was added (20 ml) to fluidize, followed by the addition of acetone (120 ml) in portions for about 1 hour and reflux for another hour. The resulting suspension was filtered and the product was dried under vacuum at 50° C. for 16 hours to give (S)-1-((3,5-bis((1,3-dihydroxypropan-2-yl)carbamoyl)-2,4,6-triiodophenyl)amino)-1-oxopropan-2-yl acetate as a white solid (19.0 g, 23.1 mmol).

Yield: 82.0%

HPLC purity: 98% (including 2% Iopamidol)

EXAMPLE 5

Preparation of (S)-1-((3,5-bis((1,3-dihydroxypropan-2-yl)carbamoyl)-2,4,6-triiodophenyl)amino)-1-oxopropan-2-yl Acetate Using Wet (S)-1-((3,5-bis(chlorocarbonyl)-2,4,6-triiodophenyl)amino)-1-oxopropan-2-yl acetate 9.86 g of wet solid, obtained as per example 3 conditions, corresponding to 8.1 g (11.4 mmol) of (S)-1-((3,5-bis(chlorocarbonyl)-2,4,6-triiodophenyl)amino)-1-oxopropan-2-yl acetate, was reacted with 2-amino-1,3-propanediol (2.6 g, 28.8 mmol) in DMA (41 ml) in the presence of triethylamine (4.06 ml, 29.0 mmol) at 50° C. for 6 hours. After complete reaction and removal of the salts, the solvent was distilled under vacuum at below 70° C. until a viscous oil was obtained. While the residue was still hot, alcohol was added (8.1 ml) to fluidize, followed by the addition of acetone (48.8 ml) in portions for about 1 hour and reflux for another hour. The resulting suspension was filtered and the product was dried under vacuum at 50° C. for 16 hours to give (S)-1-((3, 5-bis((1,3-dihydroxypropan-2-yl)carbamoyl)-2,4,6-triiodophenyl)amino)-1-oxopropan-2-yl acetate as a white solid (6.45 g, 7.84 mmol).

Yield: 69.0%

HPLC purity: 98% (including 2% Iopamidol)

EXAMPLE 6

Preparation of Iopamidol

The preparation of Iopamidol from the (S)-1-((3,5-bis((1,3-dihydroxypropan-2-yl)carbamoyl)-2,4,6-triiodophenyl)amino)-1-oxopropan-2-yl acetate obtained from the previous examples was carried out following the procedures described in the literature. 18 g (22 mmol) of the compound obtained in example 4, was added to water (36 ml) and allowed to react with sodium hydroxide in aqueous solution (1.4 g in 5 ml of water, mmol) at a temperature of below 40° C. maintaining the pH at about 11 until complete reaction. The solution was desalinated and purified using cationic and anionic exchange resins, and the water evaporated under vacuum at a temperature of below 85° C. until a thick oil was obtained and from which the product was isolated and further purified by crystallization from ethanol (102 ml) to give, after filtration and drying under vacuum at a temperature of below 80° C., high purity Iopamidol (13.0 g, 16.8 mmol).

Yield: 76.4%

$[\alpha]_{436}^{20} = -5.11°$

HPLC: Impurity B=0.002% area; Impurity C=0.004% area and Iopamidol 99.76% area.

USP Iopamidol Monograph: Impurity B=0.0011% w/w; Sum of impurities I+H=0.11% w/w; Any unspecified impurity=0.029% w/w. JP Iopamidol Monograph: Related Substances by HPLC, total impurities 0.0389% w/w.

The invention claimed is:
1. A compound, (S)-5-(2-acetoxypropanamido)-2,4,6-triiodoisophthalic acid, of formula II

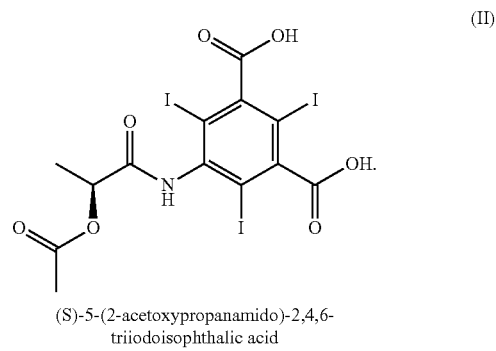 [SMILES: CC(=O)O[C@@H](C)C(=O)Nc1c(I)c(C(=O)O)c(I)c(C(=O)O)c1I]

(S)-5-(2-acetoxypropanamido)-2,4,6-triiodoisophthalic acid

2. A process to prepare a compound of formula II according to claim 1 comprising the step of acylating 5-amino-2,4,6-triiodoisophtalic acid with an (S)-1-chloro-1-oxopropan-2-yl acetate.

3. A process according to claim 2 wherein the acyl halide is used in a ratio of at least 1.5:1 relative to the 5-amino-2,4,6-triiodoisophtalic acid.

4. A process according to claim 2 wherein the acylating step is carried out in an aprotic polar solvent.

5. A process according to claim 4, wherein the aprotic polar solvent is dimethylacetamide (DMA).

6. A process according to claim 5, wherein from 1 ml to 5 ml of DMA is used per 1 gram of 5-amino-2,4,6-triiodoisophthalic acid.

7. A process according to claim 2 wherein the reaction is carried out at a temperature of from 40° C. to 60° C.

8. A process according to claim 7 wherein the temperature is maintained for a set period of time of from 5 to 9 hours.

9. A process according to claim 8 wherein, after the temperature has been maintained for the set period of time, the reaction mixture is stirred at a temperature of from 15° C. to 25° C., until conversion to the compound of formula II.

10. A process according to claim 2 wherein the solution containing the compound of formula II is added to water from which the compound of formula II may be separated by filtration.

11. A process according to claim 10 wherein the solution containing the compound of formula II is added to water in a ratio of from 5:1 to 16:1 relative to the polar aprotic solvent.

12. A process according to claim 10 wherein the solution containing the compound of formula II is added to water at a temperature of from 15° C. to 25° C.

13. A process to prepare a triiodinated contrast agent, comprising the step of converting the compound of formula II

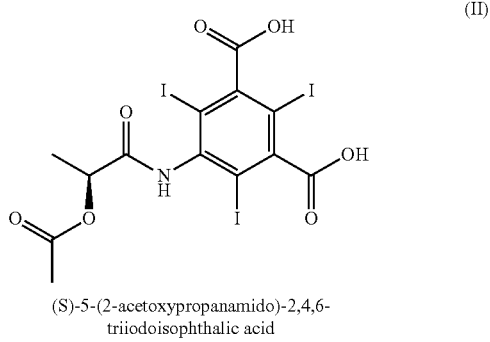 [SMILES: CC(=O)O[C@@H](C)C(=O)Nc1c(I)c(C(=O)O)c(I)c(C(=O)O)c1I]

(S)-5-(2-acetoxypropanamido)-2,4,6-triiodoisophthalic acid to the respective acid dihalide, (S)-1-((3,5-bis(halocarbonyl)-2,4,6-triiodophenyl)amino)-1-oxopropan-2-yl acetate by reaction with a halidating reagent in a polar solvent.

14. A process according to claim 13 wherein the temperature of the said reaction is set at from 25° C. to 50° C.

15. A process according to claim 13 wherein the polar solvent is acetonitrile, N-methylpyrrolidone, or DMA.

16. A process according to claim 13 wherein the polar solvent is used in a ratio of 5:1 relative to the compound of formula II.

17. A process according to claim 13 wherein the compound of formula II is converted to the respective acid dichloride, (S)-1-((3,5-bis(chlorocarbonyl)-2,4,6-triiodophenyl) amino)-1-oxopropan-2-yl acetate by reaction with a chlorinating agent.

18. A process according to claim 17 wherein the chlorinating agent is phosphorus pentachloride.

19. A process according to claim 13 wherein the reaction mixture after complete reaction is added to water in a ratio of about 2:1 relative to the quantity of the polar solvent to isolate the acid dihalide of the compound of formula II.

20. A process according to claim 13 wherein the reaction mixture after complete reaction is added to water at a temperature of from 0° C. to 10° C. to isolate the acid dihalide of the compound of formula II.

21. A process according to claim 20 wherein the acid dihalide is further purified by suspension in a mixture of water and isopropyl alcohol.

22. A process according to claim 20 wherein the acid dihalide of the compound of formula II is used directly as a wet solid without drying or as a dried solid after drying in the next chemical step.

23. A process according to claim 13, comprising an amidation step to convert the acid dihalide, (S)-1-((3,5-bis(halocarbonyl)-2,4,6-triiodophenyl)amino)-1-oxopropan-2-yl acetate to the compound of formula IV (S)-1-((3,5-bis((1,3-dihydroxypropan-2-yl)carbamoyl)-2,4,6-triiodophenyl) amino)-1-oxopropan-2-yl acetate by reaction with 2-amino-1,3-propanediol.

24. A process according to claim 23, comprising a step of acetate hydrolysis of the compound of formula IV to provide Iopamidol.

25. A process according to claim 13 wherein the iodinated contrast agent is Iopamidol.

26. A process according to claim 7 wherein the solution containing the compound of formula II is added to water from which the compound of formula II may be separated by filtration.

* * * * *

UNITED STATES PATENT AND TRADEMARK OFFICE
CERTIFICATE OF CORRECTION

| | |
|---|---|
| PATENT NO. | : 8,835,672 B2 |
| APPLICATION NO. | : 14/128782 |
| DATED | : September 16, 2014 |
| INVENTOR(S) | : Jose Manuel Galindro et al. |

Page 1 of 1

It is certified that error appears in the above-identified patent and that said Letters Patent is hereby corrected as shown below:

On the Title Page item (86),

Please correct the error of §371 (c)(1),(2),(4) Date from:

"Dec. 23, 2013" to -- Feb. 14, 2014 --.

Signed and Sealed this
Fourteenth Day of April, 2015

Michelle K. Lee
*Director of the United States Patent and Trademark Office*